: 
United States Patent [19]

Sargent et al.

[11] Patent Number: 5,905,079
[45] Date of Patent: May 18, 1999

[54] 1,2,4-TRIAZOLO[4,3-B]PYRIDAZINE DERIVATIVES AND THEIR USE

[75] Inventors: Bruce Jeremy Sargent, Nottingham, United Kingdom; Maria Isabel Fernández Fernández; Maria Aranzazu Villanueva Iñurrategui, both of Madrid, Spain

[73] Assignee: Knoll Aktiengesellschaft, Ludwigshafen, Germany

[21] Appl. No.: 08/930,864

[22] PCT Filed: Mar. 29, 1996

[86] PCT No.: PCT/EP96/01387

§ 371 Date: Oct. 7, 1997

§ 102(e) Date: Oct. 7, 1997

[87] PCT Pub. No.: WO96/32393

PCT Pub. Date: Oct. 17, 1996

[30] Foreign Application Priority Data

Apr. 8, 1995 [GB] United Kingdom .................. 9507348

[51] Int. Cl.[6] .......................... C07D 487/04; A61K 31/50
[52] U.S. Cl. ............................................. 514/248; 544/236
[58] Field of Search ................. 544/236; 514/248

[56] References Cited

U.S. PATENT DOCUMENTS

| | | | |
|---|---|---|---|
| 4,112,095 | 9/1978 | Allen, Jr. et al. ................. | 544/236 |
| 4,526,890 | 7/1985 | Peet et al. ........................ | 514/248 |
| 4,654,343 | 3/1987 | Albright et al. .................. | 514/248 |
| 5,492,909 | 2/1996 | Miyake et al. ................... | 544/236 |

FOREIGN PATENT DOCUMENTS

| | | |
|---|---|---|
| 89/01478 | 2/1989 | WIPO . |
| 95/10521 | 4/1995 | WIPO . |

*Primary Examiner*—Emily Bernhardt
*Attorney, Agent, or Firm*—Keil & Weinkauf

[57] ABSTRACT

Certain 1,2,4-triazolo(4,3-b)pyridazines of formula

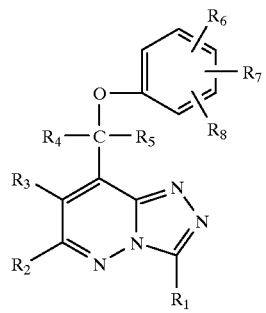

I including pharmaceutically acceptable salts thereof, wherein $R_1$–$R_8$ are as defined in the disclosure, for the treatment, prophylaxis and/or inhibition of seizures, neurological disorders such as epilepsy and/or conditions in which there is neurological damage such as stroke, brain trauma, cerebral ischemia, head injuries and hemorrhage are disclosed.

6 Claims, No Drawings

1,2,4-TRIAZOLO[4,3-B]PYRIDAZINE DERIVATIVES AND THEIR USE

This invention relates to certain 1,2,4-triazolo[4,3-b]pyridazines, to pharmaceutical compositions containing them, to processes for their preparation and to their use in the treatment and/or prophylaxis of seizures, neurological disorders such as epilepsy and/or conditions in which there is neurological damage such as stroke, brain trauma, cerebral ischaemia, head injuries and haemorrhage.

In particular the present invention provides novel compounds of formula I

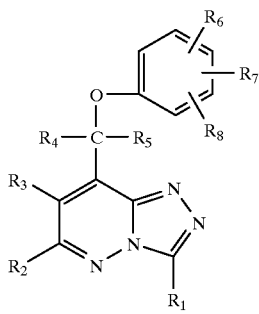

including pharmaceutically acceptable salts thereof in which:
- $R_1$ represents hydrogen, cyano, a group of formula $R_xR_yN$-(in which $R_x$ and $R_y$ independently represent hydrogen or a $C_{1-6}$alkyl group), or one of the following groups (optionally substituted with one or more of halo, cyano, hydroxy or a group of formula $R_xR_yN$ as previously defined): $C_{1-6}$alkyl, $C_{1-6}$alkoxy or $C_{1-6}$alkanoyl;
- $R_2$ and $R_3$ independently represent hydrogen or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;
- $R_4$ and $R_5$ independently represent hydrogen, $C_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl); and
- $R_6$, $R_7$ and $R_8$ independently represent hydrogen, halo, hydroxy, mercapto, cyano or one of the following groups (optionally substituted with one or more of halo, cyano, hydroxy or amino; and any nitrogen atom being optionally substituted with one or more $C_{1-6}$alkyl): $C_{1-6}$alkyl, $C_{1-6}$alkanoyl, $C_{1-6}$alkoxy, $C_{2-6}$alkoxycarbonyl, carboxy, $C_{1-6}$alkanoyloxy, $C_{1-6}$alkylthio, $C_{1-6}$alkylsulphinyl, $C_{1-6}$alkylsulphonyl, $C_{1-6}$alkylsulphonylamino, sulphamoyl, carbamoyl, $C_{2-6}$alkylcarbamoyl or $C_{1-6}$alkanoylamino.

It will be understood that any group mentioned herein which contains a chain of three or more atoms signifies a group in which the chain may be straight or branched. For example, an alkyl group may comprise propyl which includes n-propyl and isopropyl and butyl which includes n-butyl, sec-butyl, isobutyl and tert-butyl. The total number of carbon atoms is specified herein for certain substituents, for example $C_{1-6}$alkyl signifies an alkyl group having from 1 to 6 carbon atoms. The term 'halo' as used herein signifies fluoro, chloro, bromo and iodo. The term optionally substituted as used herein, unless immediately followed by a list of one or more substituent group or groups, means optionally substituted with one or more of halo, cyano, hydroxy, amino or $C_{1-6}$alkyl. When the phenyl ring substituents $R_6$, $R_7$ and $R_8$ are other than hydrogen, the substituent may replace any hydrogen attached to a carbon atom in the ring and may be located at any such position of the ring, i.e. up to three of positions 2, 3, 4, 5 and/or 6.

Preferred compounds of formula I are represented by formula II

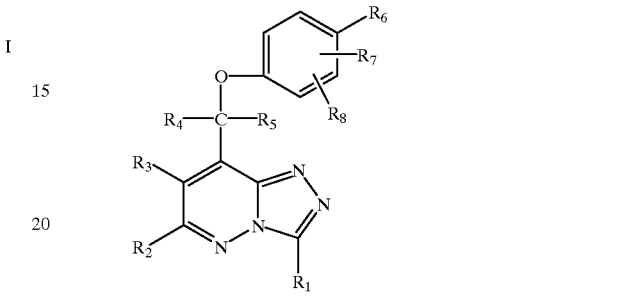

including pharmaceutically acceptable salts thereof in which:
- $R_1$ represents hydrogen, or a $C_{1-4}$alkyl group;
- $R_2$ and $R_3$ each represent hydrogen;
- $R_4$ represents hydrogen;
- $R_5$ represents hydrogen or a $C_{1-4}$alkyl group;
- $R_6$ represents halo; and
- $R_7$ and $R_8$ each represent hydrogen.

In preferred compounds of formula II, $R_1$ represents hydrogen or methyl; $R_2,R_3,R_4,R_7$ and $R_8$ each represent hydrogen; $R_5$ represents methyl; and $R_6$ represents chloro or fluoro.

Specific compounds of formula I are:
- 8-[1-(4-chlorophenoxy)ethyl]-1,2,4-triazolo[4,3-b]-pyridazine;
- 8-[1-(4-fluorophenoxy)ethyl]-1,2,4-triazolo[4,3-b]-pyridazine;
- 8-[1-(4-chlorophenoxy)ethyl]-3-methyl-1,2,4-triazolo[4,3-b]pyridazine;

and pharmaceutically acceptable salts thereof in the form of individual enantiomers, racemates or other mixtures of enantiomers.

Certain compounds of formula I may form salts of formula I with organic or inorganic acids and/or bases. As stated above, reference herein to compounds of formula I includes all salts of formula I which are pharmaceutically acceptable.

Particularly suitable salts of formula I which are pharmaceutically acceptable are those which may be formed from acids and, for example, comprise salts of inorganic acids (for example salts of hydrochloric, hydrobromic, hydriodic, nitric, sulphuric and/or phosphoric acids), salts of organic acids (for example salts of maleic, acetic, citric, fumaric, tartaric, succinic, benzoic, pamoic, palmitic, methylsulphuric and/or dodecanoic acids) and/or salts of acidic amino acids (for example salts of glutamic acids). Such salts include all pharmaceutically acceptable salts formed from multivalent acids (for example bicarbonate and/or orthophosphate salts).

It will be appreciated that such salts of formula I provided they are pharmaceutically acceptable may be used in therapy in place of corresponding compounds of formula I. Such salts may be prepared by reacting corresponding compounds of formula I with a suitable acid or base in a conventional manner.

Certain compounds of formula I may exist in more than one physical form (for example different crystal forms) and the present invention includes each physical form (for example each crystal form) of compounds of formula I and mixtures thereof.

Certain compounds of formula I may also exist in the form of solvates (for example hydrates) and the present invention includes each solvate of compounds of formula I and mixtures thereof. The degree of solvation may be non-stoichiometric. If the solvent is water the hydrate may be, for example, a hemihydrate, a monohydrate or a dihydrate.

It will be appreciated by those skilled in the art that certain compounds of formula I may contain one or more chiral centre or centres and exist in different optically active forms. Thus, for example, compounds of formula I in which $R_4$ and $R_5$ are different contain a chiral centre at the asymmetrically substituted carbon atom. When a compound of formula I contains a single chiral centre it may exist in two enantiomeric forms. The present invention includes each enantiomer of compounds of formula I and mixtures thereof.

The enantiomers may be obtained by methods known to those skilled in the art. Such methods typically include one or more of any of the following: resolution via formation of diastereoisomeric salts or complexes which may be separated, for example, by crystallisation;

formation of diastereoisomeric derivatives or complexes which may be separated (for example, by crystallisation, gas-liquid or liquid chromatography), followed by the liberation of the desired enantiomer from the separated derivative;

selective derivatisation of one enantiomer by reaction with an enantiomer-specific reagent (for example enzymatic esterification, oxidation or reduction), followed by separation of the modified and unmodified enantiomers;

use of gas-liquid or liquid chromatography in a chiral environment (for example on a chiral support such as silica gel with a bound chiral ligand and/or in the presence of a chiral solvent); asymmetric synthesis of a specific enantiomer using optically active reagents, substrates, catalysts, solvents and/or enzymatic processes; and asymmetric transformation of one enantiomer into the other.

When compounds of formula I contain more than one chiral centre they may exist in diastereoisomeric forms. The diastereoisomers may be separated by methods known to those skilled in the art, for example by chromatography or crystallisation and individual enantiomers within the diastereoisomers may be separated as described above. The present invention includes each diastereoisomer of compounds of formula I and mixtures thereof.

It will be appreciated that where the active moiety is transformed by the separation procedures described above, a further step may be required to convert the transformation product back to the active moiety.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. For example, if $R_3$, $R_4$ and/or $R_5$ are bulky groups there may be restricted rotation about one or more single bond or bonds due to steric hindrance, or if $R_4$ and $R_5$ and the carbon atom to which they are attached represent cycloalkylidene the ring may exist in more than one stable conformation. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

The present invention also relates to pharmaceutical compositions comprising a therapeutically effective amount of a compound of formula I together with a pharmaceutically acceptable diluent or carrier. Such pharmaceutical compositions may be used for the treatment and/or prophylaxis of the diseases, disorders and/or conditions described herein. Preferably pharmaceutical compositions of the present invention comprise the preferred and/or particularly preferred compounds of formula I described herein. Specific compounds which may be incorporated into the pharmaceutical compositions of the present invention are the compounds exemplified herein.

As used herein, the term "active compound" denotes one or more compound or compounds of formula I and mixtures thereof.

In therapeutic use, the active compound may be administered orally, rectally, parenterally or topically. Thus the therapeutic compositions of the present invention may take the form of any of the known pharmaceutical compositions for such methods of administration. The compositions may be formulated in a manner known to those skilled in the art, to give a controlled release, for example rapid release or sustained release, of the active compound. Pharmaceutically acceptable carriers suitable for use in such compositions are well known in the art of pharmacy. The compositions may contain from about 0.1% to about 99% by weight of active compound and are generally prepared in unit dosage form. Preferably the unit dosage of active compound is from about 1 mg to about 1000 mg. The excipients used in the preparation of these compositions are the excipients known in the pharmacist's art.

Preferably compositions of the present invention are administered orally in the known pharmaceutical forms for such administration. Dosage forms suitable for oral administration may comprise tablets, pills, capsules, caplets, granules, powders, extrudates, elixirs, syrups, solutions and/or suspensions (for example in aqueous and/or oily media).

Solid oral dosage forms, for example tablets, may be prepared by mixing the active compound with one or more of the following ingredients and/or mixtures thereof:

inert diluents (for example lactose, powdered sugar, pharmaceutical grade starch, kaolin, mannitol, calcium phosphate and/or calcium sulphate);

disintegrating agents (for example maize starch, methyl cellulose, agar, bentonite, cellulose, wood products, alginic acid, guar gum, citrus pulp, carboxymethylcellulose and/or sodium lauryl sulphate);

lubricating agents (for example magnesium stearate, boric acid, sodium benzoate, sodium acetate, sodium chloride, leucine and/or polyethylene glycol);

binders (for example starch, gelatin, sugars [such as sucrose, molasses and/or lactose], and/or natural and/or synthetic gums [such as acacia, sodium alginate, extract of Irish moss, carboxymethylcellulose, methylcellulose, ethylcellulose, polyethylene glycol, waxes, micro-crystalline cellulose and/or polyvinylpyrrolidone]);

colouring agents (for example conventional pharmaceutically acceptable dyes);

sweetening and/or flavouring agents;

preservatives;

one or more pharmaceutically acceptable couple or couples (for example those comprising an acid and a carbonate and/or bicarbonate salt), which effervesce to aid dissolution if the solid dosage form is added to water; and other optional ingredients known in the art to permit production of oral dosage forms by known methods such as tabletting.

Solid oral dosage forms may be formulated in a manner known to those skilled in the art so as to give a sustained release of the active compound. Enteric coated, solid oral dosage forms comprising compositions of the present invention may be advantageous, depending on the nature of the active compound. Various materials, for example shellac and/or sugar, may be present as coatings, or to otherwise modify the physical form of the oral dosage form. For example tablets or pills may, if desired, be provided with enteric coatings by known methods, for example by the use of cellulose acetate phthalate and/or hydroxy propyl methylcellulose phthalate.

Capsules and/or caplets (for example hard or soft gelatin capsules) comprising the active compound (with or without added excipients such as a fatty oil), may be prepared by conventional means and, if desired, provided with enteric coatings in a known manner. The contents of the capsule and/or caplet may be formulated using known methods to give sustained release of the active compound.

Liquid oral dosage forms comprising compositions of the present invention may be an elixir, suspension and/or syrup (for example, aqueous suspensions containing the active compound in an aqueous medium in the presence of a non-toxic suspending agent [such as sodium carboxymethylcellulose] and/or oily suspensions containing the active compound in a suitable vegetable oil [such as arachis oil and/or sunflower oil]). Liquid oral dosage forms may also comprise one or more sweetening agent, flavouring agent, preservatives and/or mixtures thereof.

The active compound may be formulated into granules and/or powders with or without additional excipients. The granules and/or powders may be ingested directly by the patient or they may be added to a suitable liquid carrier (for example water) before ingestion. The granules and/or powders may contain disintegrants (for example a pharmaceutically acceptable effervescent couple formed from an acid and a carbonate and/or bicarbonate salt) to facilitate dispersion in the liquid medium.

Preferably each of the above oral dosage forms may contain from about 1 mg to about 1000 mg, more preferably from about 5 mg to about 500 mg (for example 10 mg, 50 mg, 100 mg, 200 mg, or 400 mg) of the active compound.

Pharmaceutical compositions of the present invention may be administered rectally in the known pharmaceutical forms for such administration (for example, suppositories with hard fat, semi-synthetic glyceride, cocoa butter and/or polyethylene glycol bases).

Pharmaceutical compositions may also be administered parenterally (for example subcutaneously, intramuscularly, intradermally and/or intravenously [such as by injection and/or infusion]) in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]) Optionally one or more of the following pharmaceutically acceptable adjuvants suitable for parenteral administration may be added to parenteral dosage forms: local anaesthetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Pharmaceutical compositions of the present invention may be administered topically, the compositions comprising a matrix in which the active compound is dispersed so that the active compound is held in contact with the skin in order to administer the compound transdermally. The amount of active compound comprising a topical formulation should be such that a therapeutically effective amount of the active compound would be delivered during the period of time which the topical formulation is intended to be on the skin.

A suitable transdermal composition may be prepared by mixing or dispersing the active compound in a topical vehicle together with a potential transdermal accelerant such as dimethyl sulphoxide and/or propylene glycol. The topical vehicle may be a pharmaceutically acceptable foam, paste, salve, lotion, cream, ointment, emulsion and/or gel base; and/or a composition suitable for application in the form of a spray. Topical vehicles may also comprise topical delivery devices such as cataplasms, poultices, patches and/or impregnated bandages.

A suitable cream may be prepared by incorporating the active compound in petrolatum and/or light liquid paraffin which is then dispersed in an aqueous medium using surfactants. An ointment may be prepared by mixing the active compound with a mineral oil, petrolatum and/or a wax (such as paraffin wax and/or beeswax). A gel may be prepared by mixing the active compound with a gelling agent (such as basified Carbomer BP) in the presence of water. A clear gel may comprise a clarifying agent (for example a denaturated alcohol [such as denaturated ethanol]).

Preferably pharmaceutical compositions of the present invention for topical administration may also comprise a thickening agent and/or may further comprise a pH adjusting agent that is compatible with the active compound. Preferably the pH adjusting agent is present in an amount which is sufficient to activate the thickening agent, if present, and which will keep the pH of the composition within a pharmaceutically and cosmetically acceptable range that will not damage the skin. More preferably the pH of the composition is from about 5.0 to about 9.0.

If the pharmaceutical composition of the present invention for topical administration is an emulsion, such an emulsion may be either an oil-in-water or a water-in-oil emulsion. The oil phase of such an emulsion may comprise one or more of the following ingredients: hydrocarbon oils, waxes, natural oils, silicone oils, fatty acid esters, fatty alcohols and/or mixtures thereof. Pharmaceutical compositions of the present invention that are emulsions can be prepared by using an emulsifier or mixture of emulsifiers for use in water-in-oil or oil-in-water emulsions and acceptable for use in topical pharmaceutical compositions. Such emulsifiers may comprise any suitable emulsifier or emulsifiers well known to those skilled in the art and/or mixtures thereof.

When a pharmaceutical composition of the present invention for topical administration is not an emulsion, an emulsifying ingredient or surfactant may still be present as a surface active agent to promote greater therapeutic activity in the pharmaceutical composition when it is applied topically.

Pharmaceutical compositions of the present invention for topical administration may additionally comprise another component or components well known to those skilled in the art for example: emulsion stabilisers, emulsion stabilising salts, sequestrants, emollients, humectants, moisturisers, film formers, perfumes, preservatives, colourings and/or mixtures thereof.

The active compound may also be administered by continuous infusion either from an external source (for example by intravenous infusion) or from a source of the active compound placed within the body. Internal sources include implanted reservoirs containing the active compound to be infused from which the active compound is continuously released (for example by osmosis) or implants. Implants may be liquid such as a suspension or solution in a pharmaceutically acceptable solvent of the active compound to be infused (for example in the form of a very sparingly water-soluble derivative such as a dodecanoate salt and/or ester in an oil). Implants may also be solid in the form of an implanted support (for example a synthetic resin and/or waxy material) for the active compound to be infused. The support may be a single body containing all the active compound or a series of several bodies each containing part of the active compound to be delivered. The amount of active compound present in an internal source should be such that a therapeutically effective amount of the active compound is delivered over a long period of time.

In some formulations it may be beneficial to use the active compound, or pharmaceutical compositions containing the active compound, in the form of particles of very small size, for example as obtained by fluid energy milling.

In the compositions of the present invention described herein the active compound may, if desired, be associated with other compatible pharmacologically active ingredients.

An aspect of the present invention comprises use of a compound of formula I and/or a pharmaceutical composition or compositions comprising a therapeutically effective amount of a compound of formula I in a method of therapy for animals. As used herein the term animal is to be construed as including human beings. Preferred patients for the therapy described herein comprise mammals, more preferably human beings.

Compounds of formula I are indicated for therapeutic use as medicaments for the treatment, prophylaxis and/or inhibition of seizures, neurological disorders such as epilepsy, and/or conditions in which there is neurological damage, such as stroke, brain trauma, cerebral ischaemia, head injuries and haemorrhage. The therapeutic activity of compounds falling within the disclosure of formula I has been demonstrated by means of various in vivo pharmacological tests in standard laboratory animals. Such tests include those tests of anti-convulsant activity in mice described below.

It will be appreciated that the term therapy as used herein includes both treatment and/or prophylactic use of the active compound and/or one or more pharmaceutical composition or compositions comprising a therapeutically effective amount of the active compound. For example, in the present invention prophylactic use of the active compound comprises prevention of the onset of seizures, and/or neurological disorders such as epilepsy, and/or use as neuroprotective agents to protect against conditions in which there is neurological damage, such as stroke, brain trauma, cerebral ischaemia, head injuries and haemorrhage, in animals including human beings.

Accordingly, a further aspect of the present invention provides a method of treatment, prophylaxis and/or inhibition of seizures, neurological disorders such as epilepsy and conditions in which there is neurological damage, such as stroke, brain trauma, cerebral ischaemia, head injuries and haemorrhage, in mammals including human beings, which comprises the administration of a therapeutically effective amount of a compound of formula I to a mammal in need thereof.

While the precise mechanism of action of the active compound is unknown at present, it is believed that the pharmacological activity of the active compound in the conditions outlined herein may arise from the ability to potentiate transmission of the neurotransmitter gamma-amino butyric acid (GABA-A) and/or the ability to activate potassium ion ($K^+$) channels in neurones. However, the present invention should not be considered limited to the active compound having such pharmacological ability.

Whilst the precise amount of the active compound administered in the therapeutic methods outlined above will depend on a number of factors (for example the severity of the condition, the age and/or past medical history of the patient) and always lies within the sound discretion of the administering pharmacist, physician and/or veterinary practitioner, a suitable daily dose of the active compound for administration to human beings, is generally from about 1 mg to about 1000 mg, more usually from about 5 mg to about 500 mg, given in a single dose or in divided doses at one or more times during the day. Oral administration is preferred.

The active compound may be used in adjunctive therapy with one or more other compound or compounds having activity in the treatment, prophylaxis and/or inhibition of seizures, neurological disorders such as epilepsy, and/or conditions in which there is neurological damage, such as stroke, brain trauma, cerebral ischaemia, head injuries and haemorrhage, in animals including human beings. The active compound and/or one or more pharmaceutical composition or compositions comprising a therapeutically effective amount of the active compound may be used to provide a local and/or systemic therapeutic effect.

A still further aspect of the present invention provides use of a compound of formula I in the preparation of a medicament. Preferably the medicament is useful in the treatment, prophylaxis and/or inhibition of seizures, neurological disorders such as epilepsy and conditions in which there is neurological damage, such as stroke, brain trauma, cerebral ischaemia, head injuries and haemorrhage, in mammals including human beings.

Processes for the preparation of compounds of formula I will now be described. These processes form a further aspect of the present invention.

Compounds of formula I may be prepared by reacting compounds of formula III

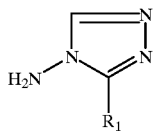

III with compounds of formula IV

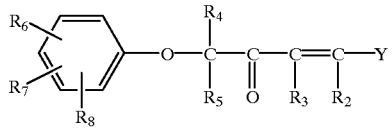

IV in which Y is a suitable leaving group, for example Cl, —N(Me)₂ or alkoxy.

Compounds of formula I may be prepared by reacting compounds of formula V

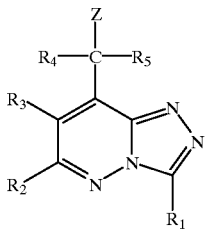

V in which Z is a suitable leaving group, for example Br or Cl, with anions of formula VI

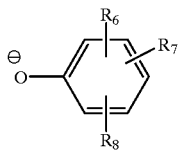

VI

Compounds of formula IV in which Y is —N(Me)₂ may be prepared by reacting compounds of formula VII

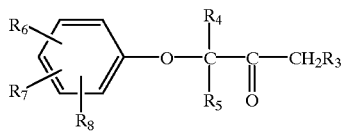

VII with compounds of formula VIII

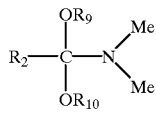

VIII in which $R_9$ and $R_{10}$ independently represent $C_{1-6}$alkyl, or if $R_2$ is H, with 'Gold's reagent' which is a compound of formula $Me_2NCH=NCH=NMe_2Cl$.

Compounds of formula V may be prepared by reacting compounds of formula III with compounds of formula IX

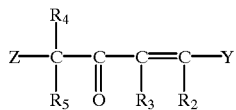

IX

Compounds of formula IX in which Y is —N(Me)₂ may be prepared by reacting compounds of formula $ZCR_4R_5COCH_2R_3$ with compounds of formula VIII, or if $R_2$ is H, with Gold's reagent.

Compounds of formula V in which Z is halo, may be prepared by reacting compounds of formula X

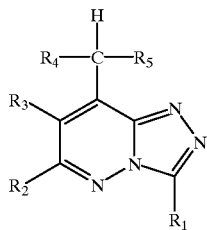

X with a halogenating agent, for example N-bromosuccinimide, optionally in the presence of a catalyst, for example benzoylperoxide.

Compounds of formula X may be prepared by reacting compounds of formula III with compounds of formula XI

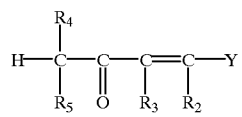

XI

Compounds of formula XI in which Y is —N(Me)₂ may be prepared by reacting compounds of formula $CHR_4R_5COCH_2R_3$ with compounds of formula VIII, or if $R_2$ is H, with Gold's reagent.

Compounds of formula X in which $R_2$ represents hydrogen may also be prepared by reducing compounds of formula XII

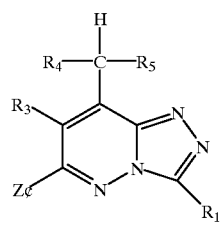

XII in which Z' is a leaving group, for example a halo such as Cl, with a reducing agent, for example hydrogen, with a Palladium/carbon catalyst.

Compounds of formula XII may be prepared by reacting compounds of formula XIII

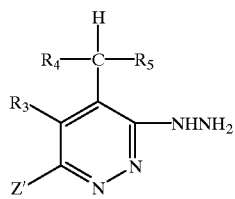

XIII with compounds of formula $R_1C(OR)_3$ in which R represents a $C_{1-4}$alkyl group, for example methyl or ethyl.

Compounds of formula XIII may be prepared by reacting compounds of formula XIV

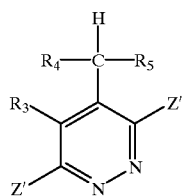

XIV with hydrazine hydrate ($N_2H_4$).

Compounds of formula XIV may be prepared by methods described in the art (Org. Prep. Proced. Int.20 (1–2),117–21 (1988).

Compounds of formula I may be prepared by coupling alcohols of formula XV

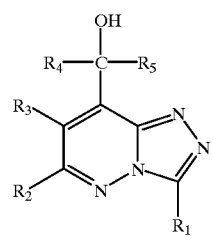

XV with phenols of formula XVI

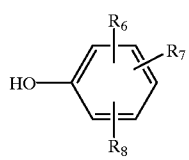

XVI in the presence of a coupling agent which, for example, in the 'Mitsunobu' reaction is diethylazodicarboxylate with triphenylphosphine.

If $R_4$ and $R_5$ are different the stereospecific 'Mitsunobu' reaction provides a route to single enantiomers of compounds of formula I.

Compounds of formula V in which Z is halo, may be prepared by reacting alcohols of formula XV with a halogenating agent, for example thionyl chloride; or triphenylphosphine with bromine.

Alcohols of formula XV in which $R_5$ is H may be prepared by reducing compounds of formula XVII

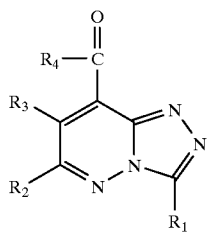

XVII with a reducing agent, for example sodium borohydride, or optionally with a chiral reducing agent to afford single enantiomers of alcohols of formula XV.

Compounds of formula XVII may be prepared by using a cleaving agent to cleave compounds of formula XVIII

XVIII $$R_4-\underset{\underset{L_2}{|}}{\overset{\overset{L_1}{|}}{C}}-\text{[pyridazine-triazole]}$$

in which $L_1$ and $L_2$ are alkoxy or alkylthio; or together with the carbon atom to which they are attached represent a dioxolane, dioxane, dithiolane or dithiane ring. For example when compounds of formula XVIII are dithiolanes or dithianes the cleaving agent may be silver nitrate with N-chlorosuccinimide; or ceric ammonium nitrate. When $L_1$ and $L_2$ are both methoxy the cleaving agent may be a suitable Amberlyst® ion exchange resin available commercially from Aldrich Chemicals.

Compounds of formula X in which $R_5$ is H, may be prepared by reducing compounds of formula XVII.

Compounds of formula XVIII may be prepared by reacting compounds of formula III with compounds of formula XIX

XIX $$R_4-\underset{\underset{L_2}{|}}{\overset{\overset{L_1}{|}}{C}}-\underset{\overset{\|}{O}}{C}-\underset{\overset{|}{R_3}}{C}=\underset{\overset{|}{R_2}}{C}-Y$$

Compounds of formula XIX in which Y is $-N(Me)_2$ may be prepared by reacting compounds of formula XX

XX $$R_4-\underset{\underset{L_2}{|}}{\overset{\overset{L_1}{|}}{C}}-\underset{\overset{\|}{O}}{C}-CH_2R_3$$

with compounds of formula VIII, or if $R_2$ is H, with Gold's reagent.

Alcohols of formula XV may be prepared by reacting compounds of formula V with hydroxide ions, for example using a suitable alkali.

Alcohols of formula XV may be prepared by hydrolysing compounds of formula XXI

XXI

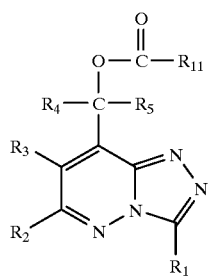

in which $R_{11}$ is optionally substituted alkyl or optionally substituted aryl with, for example, potassium carbonate. The hydrolysis may be conducted under conditions which afford single enantiomers of alcohols of formula XV, for example by use of an appropriate hydrolytic enzyme.

Compounds of formula XXI may be prepared by reacting compounds of formula V with carboxylate anions of formula $R_{11}CO_2^-$, which may be any acylate group (for example acetate or benzoate); and may also be a chiral group (for example mandelate $[PhCH(OH)CO_2^-]$). If single enantiomers of $R_{11}CO_2$ are used to prepare compounds of formula XXI in which $R_4$ and $R_5$ are different, mixtures of diastereomeric esters may be formed, which may be separated (for example by selective recrystallisation) and the desired diastereoisomers hydrolysed to afford single enantiomers of alcohols of formula XV.

Compounds of formula XXI may be prepared by reacting compounds of formula XV with carboxylic acids of formula $R_{11}CO_2H$ in the presence of a coupling agent, for example dicyclohexylcarbodiimide; or triphenylphosphine with diethylazodicarboxylate.

Compounds of formula XXI may be prepared by reacting compounds of formula III with compounds of formula XXII

XXII

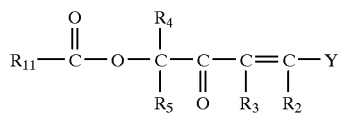

Compounds of formula XXII in which Y is $-N(Me)_2$ may be prepared by reacting compounds of formula XXIII

XXIII

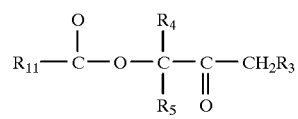

with compounds of formula VIII, or if $R_2$ is H, with Gold's reagent.

Compounds of formula XXIII may be prepared by reacting compounds of formula XXIV

XXIV

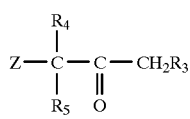

with anions of formula $R_{11}CO_2^-$.

Compounds of formula I in which at least one of $R_6$, $R_7$ and/or $R_8$ is selected from alkylsulphinyl and alkylsulphonyl, may be prepared by oxidising compounds of formula I in which $R_6$, $R_7$ and/or $R_8$ are alkylthio, using, for example, peracetic acid or 3-chloroperbenzoic acid.

Compounds of formula I in which $R_3$ is H may be prepared by reducing compounds of formula XXV

XXV

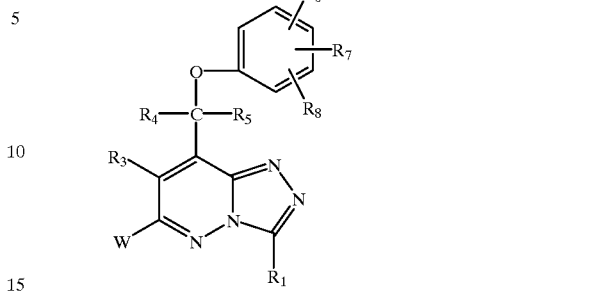

in which W is a suitable leaving group, for example halo, using a reducing agent. If W is halo, the reducing agent may be, for example, hydrogen optionally in the presence of a catalyst, for example, palladium.

If $R_4$ and $R_5$ are different this provides routes to single enantiomers of compounds of formula I.

Compounds of formula XXV in which W is halo, may be prepared by reacting compounds of formula XXV in which W is hydroxy with a halogenating agent, for example phosphoryl chloride.

Compounds of formula XXV in which $R_3$ is H and W is hydroxy may be prepared by reacting compounds of formula III with compounds of formula XXVI

XXVI

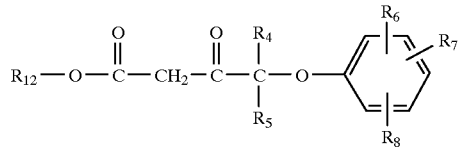

in which $R_{12}$ represents $C_{1-6}$alkyl.

The anticonvulsant activity of compounds of formula I was demonstrated by the following pharmacological tests.

The first test involved observing the ability of the compound of formula I to antagonise myoclonic seizures induced in mice by the administration of (+)-bicuculline (see Buckett W. R.; J. Pharmacol. Meth.; 1981; 5; 35–41). Bicuculline, a selective gamma-amino butyric acid-A (GABA-A) receptor antagonist, induces a characteristic convulsive syndrome when administered intravenously. The syndrome can be prevented by anti-epileptic drugs known to potentiate GABA neuro-transmission. Hereinafter, this test is referred to as 'BICM'.

In the BICM experiments groups of female mice in the weight range 25 to 30 grammes were used. Two hours prior to the experiment food was withdrawn, but the mice continued to have free access to water. The mice were divided into two groups, a control group and a test group to which compounds of formula I or II would be administered. The control group received an oral dose of 10 ml/kg of a vehicle of 1% aqueous methyl cellulose solution. The test group received orally, suspended in the same dose of the methylcellulose vehicle, a compound of formula I at a dose of either 100 mg/kg for initial testing or, if enough compound was available, at a range of doses to determine an $ED_{50}$ (see below). One hour after administration of all drugs (+)-bicuculline at a dose of 0.55 mg/kg was administered intravenously into a tail vein to all the mice in both groups. Such a dose of (+)-bicuculline would generally be expected to induce a seizure in the mice.

During the following two minutes each group of mice was observed, the number of mice in each group exhibiting convulsions was recorded and thus the percentage of mice in the test group in which seizures had been inhibited was determined. The greater the anticonvulsant activity of the compound of formula I, the higher was the percentage recorded in the BICM test.

If results at more than one dose were available, then a value for the dose inhibiting the seizures in 50% of the mice ($ED_{50}$) was calculated from the regression straight line plot of the percentage of mice in which seizures were inhibited against the dose of the compound of formula I administered.

The second test of anticonvulsant activity involved observing the ability of a compound of formula I or II to inhibit seizures in mice induced by a maximal electroshock. Hereinafter, this test is referred to as 'MESM'.

In the MESM experiments, groups of male mice in the weight range 25 to 30 grammes had free access to food and water until the start of the experiment. The mice were divided into two groups, a control group and a test group to which compound of formula I would be administered. The control group received an oral dose of 10 ml/kg of a vehicle of 1% aqueous methyl cellulose solution. The test group received orally, suspended in the same dose of the methylcellulose vehicle, a compound of formula I or II at a dose of either 100 mg/kg for initial testing or, if enough compound was available, at a range of doses to determine an $ED_{50}$ (see below). One hour after administration of all drugs an electroshock of duration 1.0 second was administered to all the mice in both groups through ear clip electrodes moistened with saline. The electroshock had an intensity of 99 mA, frequency of 50 Hz and pulse width of 0.4 ms. Such a shock would generally be expected to induce a seizure in the mice.

During the following two minutes the mice in each group were observed, the number of mice in each group exhibiting tonic hind limb extension was recorded and thus the percentage of mice in which seizures had been inhibited was determined. The greater the anticonvulsant activity of the compound of formula I, the higher was the percentage recorded in the MESM test.

If results at more than one dose were available, then a value for the dose inhibiting the seizures in 50% of the mice ($ED_{50}$) was calculated from the regression straight line plot of the percentage of mice in which seizures were inhibited against the dose of the compound of formula I administered.

The compounds of formula I described hereinafter in the Examples have been found to have anticonvulsant activity in at least one of the BICM and/or MESM tests.

The invention will now be illustrated by the following non-limiting examples. The final product of each example was characterised using one or more of the following techniques: elemental analysis; infrared spectroscopy; nuclear magnetic resonance spectroscopy;

gas-liquid chromatography; and liquid chromatography. Temperatures are given in degrees Celsius.

EXAMPLE 1 a) A mixture of 3-(4-chlorophenoxy)-2-butanone (34.50 g) and N,N-dimethylformamide dimethylacetal (20.70 g) was heated under argon in an oil bath at 120° C. for 13 hours. The methanol produced in the reaction was removed under reduced pressure and the residual oil was triturated with n-hexane. The solid was collected by filtration and washed with cold diethyl ether to give 4-(4-chlorophenoxy)-1-(dimethylamino)-1-penten-3-one. Yield 32.50 g.

b) A solution of 4-(4-chlorophenoxy)-1-(dimethylamino)-1-penten-3-one (14.5 g) in glacial acetic acid (100 ml) was added dropwise to a solution of 4-amino-1,2,4-triazole (5.0 g) in glacial acetic acid (100 ml). The solution was boiled under reflux for 4 hours and then poured into water (400 ml). The mixture was extracted with toluene. The combined organic extracts were washed with 10% sodium bicarbonate solution, then with water, dried over anhydrous magnesium sulphate, filtered, and evaporated under reduced pressure. Flash column chromatography of the residue on silica gel, using ethyl acetate/petroleum ether 1:1 as the mobile phase, afforded 1.52 g of 8-[1-(4-chlorophenoxy) ethyl]-1,2,4-triazolo[4,3-b]pyridazine. A pure sample was obtained by recrystallisation from a mixture of ethyl acetate and hexane, m.p. 98–99° C.

The $ED_{50}$, in the BICM test described above, for this compound was 42.3 mg/kg.

The $ED_{50}$, in the MESM test also described above, for this compound was 43.7 mg/kg.

EXAMPLE 2 a) A mixture of 3-(4-fluorophenoxy)-2-butanone (18.72 g) and N,N-dimethylformamide dimethylacetal (12.5 g) was heated under argon in an oil bath at 120° C. for 14 hours. The methanol produced in the reaction was removed under reduced pressure and the residual oil was precipitated with cold hexane and kept at 4° C. overnight to give 4-(4-fluorophenoxy)-1-(dimethylamino)-1-penten-3-one as an orange solid. Yield 19.97 g.

b) A solution of 4-(4-fluorophenoxy)-1-(dimethylamino)-1-penten-3-one (11 g) in glacial acetic acid (80 ml) was added dropwise to a solution of 4-amino-1,2,4-triazole (4.0 g) in glacial acetic acid (83 ml). The solution was boiled under reflux for 2 hours then cooled to room temperature and poured over water (300 ml). The mixture was extracted with toluene. The combined organic extracts were washed with 10% sodium bicarbonate solution then with water, dried over anhydrous magnesium sulphate, filtered and evaporated under reduced pressure.

Flash column chromatography of the residue on silica gel, using ethyl acetate/petroleum ether 1:1 afforded 0.9 g of 8-[1-(4-fluorophenoxy)ethyl]-1,2,4-triazolo[4,3-b] pyridazine, which was recrystallised from a mixture of ethyl acetate and hexane, m.p. 103–104° C.

The $ED_{50}$, in the BICM test described above, for this compound was 21.2 mg/kg.

The $ED_{50}$, in the MESM test also described above, for this compound was 52.2 mg/kg.

EXAMPLE 3 a) A mixture of 3,6-dichloro-4-ethylpyridazine (2 g) and hydrazine hydrate (0.6 g) was boiled under reflux for 1 hour.

The mixture was allowed to reach room temperature and a gum precipitated, which was separated and triturated with cold hexane to give 6-chloro-4-ethyl-3-hydrazinopyridazine as a solid. Yield 1.85 g.

b) A mixture of crude 6-chloro-4-ethyl-3-hydrazinopyridazine (8 g; made in a similar manner to that described above) and triethylorthoacetate (22.1 g) was boiled under reflux with stirring for 3 hours. A precipitate separated on cooling, this was collected, washed with hexane and subjected to flash column chromatography on silica gel, using ethyl acetate:hexane 9:1 as eluent. This afforded 6-chloro-8-ethyl-3- methyl-1,2,4-triazolo[4,3-b]pyridazine (1.95 g), m.p. 80–85° C., which was used without further purification.

c) 10% Palladium/carbon catalyst (0.5 g) was suspended in methanol (10 ml) and a mixture of 6-chloro-8-ethyl-3-methyl-1,2,4-triazolo[4,3-b]pyridazine (1.95 g) dissolved in methanol (25 ml) and 25% ammonium hydroxide (2 ml) was added. This total mixture was hydrogenated at 15 psi for 40 minutes with stirring until the pressure of the mixture remained constant. It was then filtered through Celite and the solvent removed. The residue was subjected to flash column chromatography using ethyl acetate:hexane 9:1 as solvent. This afforded 3-methyl-8-ethyl-1,2,4-triazolo[4,3-b] pyridazine (0.63 g), m.p. 75–79° C.

d) A mixture of crude 3-methyl-8-ethyl-1,2,4-triazolo[4,3-b]pyridazine (0.6 g) was dissolved in anhydrous carbon tetrachloride (40 ml) and N-bromosuccinimide (0.66 g) with a catalytic amount of benzoylperoxide. The total mixture was stirred at room temperature for 45 minutes and then boiled under reflux for 2 hours. The solvent was eliminated at reduced pressure and water (100 ml) was added to the residual oil. The product was extracted with ethyl acetate. The organic layer was washed with 5% aqueous sodium bicarbonate solution, then with water, dried with sodium sulphate, filtered and concentrated to dryness. The residual oil was purified by flash chromatography on silica gel using ethyl acetate as eluent to give 8-(1-bromoethyl)-3-methyl-1,2,4-triazolo[4,3-b]pyridazine as a solid. Yield 0.41 g, m.p. 125–128° C.

e) p-Chlorophenol (0.25 g) was added to a suspension of sodium hydride (0.08 g) in anhydrous dimethylformamide (5 ml). The resultant mixture was stirred at room temperature for 30 minutes then 8-(1-bromoethyl)-3-methyl-1,2,4-triazolo[4,3-b]pyridazine (0.38 g), in dimethylformamide (20 ml), was added dropwise and the mixture stirred for 1 hour. The reaction mixture was concentrated to dryness and the residue dissolved in dichloromethane (50 ml). The solution was washed with 5% aqueous sodium hydroxide and then with water. The organic layer was separated and dried with sodium sulphate, filtered and concentrated to dryness. The white solid obtained was recrystallized from ethyl acetate:hexane to give 8-[1-(4-chlorophenoxy)ethyl]-3-methyl-1,2,4-triazolo[4,3-b]pyridazine. m.p. 158–160° C.

The percentage free from seizures, in the BICM test for this compound was 60% at a dosage of 100 mg/kg.

PHARMACEUTICAL EXAMPLES

Example U

Tablets may be prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch may be de-aggregated, blended and the resulting mixture may be granulated with a solution of the polyvinylpyrrolidone in ethanol. The dry granulate may be blended with magnesium stearate and the rest of the starch. Then the mixture may be then compressed in a tabletting machine to give tablets containing 10 mg of active compound.

Example V

Tablets may be prepared by the method of the previous Example. The tablets may be enteric-coated in a conventional manner using a solution of 20% cellulose acetate phthalate and 3% diethyl phthalate in ethanol:dichloromethane (in a 1:1 ratio by volume) as solvent.

Example W

In the preparation of capsules, 10 parts by weight of active compound and 240 parts by weight of lactose may be de-aggregated and blended. The mixture may be filled into hard gelatin capsules, each capsule containing 10 mg active compound.

Example X

In the preparation of capsules, 50 parts by weight of active compound, 300 parts by weight of lactose and 3 parts by weight of magnesium stearate may be de-aggregated and blended. The mixture may be filled into hard gelatin capsules, each capsule containing 50 mg of active ingredient.

Example Y

In the preparation of suppositories, 100 parts by weight of active compound may be incorporated in 1300 parts by weight of semi-synthetic glycerides as the suppository base and the mixture may be formed into suppositories each containing 100 mg of active ingredient.

Example Z

An ointment may be formed by incorporating 0.1 g of the active compound into a base of white soft paraffin (9.9 g) by thorough homogenization until the drug is evenly distributed. The ointment (10 g) may be packed into amber jars with screw-capped lined lids.

We claim:

1. Compounds of formula I

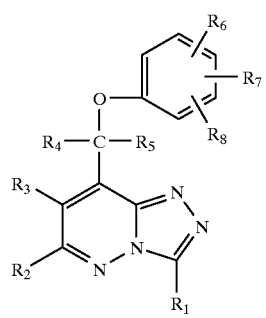

I or pharmaceutically acceptable salts thereof, in which $R_1$ represents hydrogen, cyano, a group of formula $R_xR_yN$ (in with $R_x$ and $R_y$ independently represent hydrogen or a $C_{1-6}$alkyl group), or one of the following groups (optionally substituted with one or more of halo, cyano, hydroxy or a group of formula $R_xR_yN$ as previously defined): $C_{1-6}$alkyl, $C_{1-6}$alkoxy or $C_{1-6}$alkanoyl;

$R_2$ and $R_3$ independently represent hydrogen or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent hydrogen, $C_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl); and $R_6$, $R_7$, and $R_8$ independently represent:
hydrogen, halo, hydroxy, mercapto, cyano or carboxy; sulphamoyl or carbamoyl, in which the nitrogen atom may be substituted by one or more $C_{1-6}$alkyl; or
$C_{1-6}$alkyl, $C_{1-6}$alkanoyl; $C_{1-6}$alkoxy; $C_{2-6}$alkoxycarbonyl; $C_{1-6}$alkanoyloxy; $C_{1-6}$alkylthio; $C_{1-6}$alkylsulphinyl; $C_{1-6}$alkylsulphonyl; $C_{1-6}$alkylsulphonylamino; $C_{2-6}$alkylcarbamoyl or $C_{1-6}$alkanoylamino; which may be substituted with one or more of halo, cyano, hydroxy or amino; and any nitrogen atom may be substituted with one or more $C_{1-6}$alkyl.

2. Compounds of formula I represented by formula II

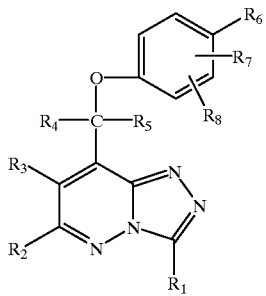

II or pharmaceutically acceptable salts thereof in which:
$R_1$ represents hydrogen, or a $C_{1-4}$alkyl group;
$R_2$ and $R_3$ each represent hydrogen;
$R_4$ represents hydrogen;
$R_5$ represents hydrogen or a $C_{1-4}$alkyl group;
$R_6$ represents halo; and
$R_7$ and $R_8$ each represent hydrogen.

3. A compound selected from:
8-[1-(4-chlorophenoxy)ethyl]-1,2,4-triazolo[4,3-b]-pyridazine;
8-[1-(4-fluorophenoxy)ethyl]-1,2,4-triazolo[4,3-b]-pyridazine; and
8-[1-(4-chlorophenoxy)ethyl]-3-methyl-1, 2,4-triazolo[4,3-b]pyridazine; and or pharmaceutically acceptable salts thereof in the form of individual enantiomers, racemates or other mixtures of enantiomers.

4. A pharmaceutical composition comprising a therapeutically effective amount of the compound of formula I as defined in claim 1 together with a pharmaceutically acceptable diluent or carrier.

5. A method of treating seizures, epilepsy, stroke, brain trauma, cerebral ischaemia, head injuries and haemorrhage, which method comprises the administration of a therapeutically effective amount of the compound defined in claim 1 to a mammal in need of such treatment.

6. A process for the preparation of compounds of formula I as defined in claim 1, said process comprising heating a compound of formula III

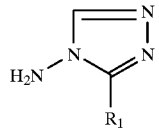

III with compounds of formula IV

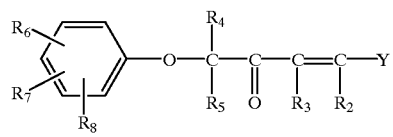

IV in which Y is a leaving group, and $R_1$–$R_8$ are as defined in claim 1 in a suitable solvent.

* * * * *